US007250539B2

(12) United States Patent
Iikubo et al.

(10) Patent No.: US 7,250,539 B2
(45) Date of Patent: Jul. 31, 2007

(54) MATERIALS AND METHODS FOR THE CONVERSION OF HYDROFLUOROCARBONS

(75) Inventors: Yuichi Iikubo, West Lafayette, IN (US); Vicki Hedrick, Brookston, IN (US); Stephen M. Brandstadter, Indianapolis, IN (US); Mitchel Cohn, West Lafayette, IN (US)

(73) Assignee: Great Lakes Chemical Corp., West Lafayette, IN (US)

( * ) Notice: Subject to any disclaimer, the term of this patent is extended or adjusted under 35 U.S.C. 154(b) by 218 days.

(21) Appl. No.: 10/331,821

(22) Filed: Dec. 30, 2002

(65) Prior Publication Data

US 2004/0127757 A1 Jul. 1, 2004

(51) Int. Cl.
*C07C 17/00* (2006.01)
*C07C 19/08* (2006.01)
*C07C 21/18* (2006.01)

(52) U.S. Cl. .................. 570/153; 570/155; 570/15; 570/161

(58) Field of Classification Search ............... 570/153, 570/155, 156, 161
See application file for complete search history.

(56) References Cited

U.S. PATENT DOCUMENTS

| 2,844,636 | A |   | 7/1958  | Haszeldine et al. ......... 260/653 |
| 5,057,634 | A | * | 10/1991 | Webster et al. ............. 570/157 |
| 5,334,783 | A | * | 8/1994  | Freudenreich et al. ...... 570/153 |
| 5,396,000 | A |   | 3/1995  | Nappa et al. ............... 870/175 |
| 5,504,248 | A |   | 4/1996  | Krusic et al. ............... 562/849 |
| 5,847,745 | A |   | 12/1998 | Shimizu et al. ............. 347/227 |
| 5,969,199 | A |   | 10/1999 | Franz et al. ................ 570/175 |

FOREIGN PATENT DOCUMENTS

| CA | 1162511 | 2/1984 |
| EP | 03 81 5021 | 7/2006 |
| RU | 220255 | 6/1968 |
| WO | WO 99/62849 | 12/1999 |
| WO | WO 01/05468 A2 | 1/2001 |
| WO | WO 04/060842 | 7/2004 |

OTHER PUBLICATIONS

International Search Report for PCT/US03/41851.
J. Kvicala, O. Paleta and V. Dedek, *Preparation of Perhalogenated Chlorofluoropropanes by Halogen Exchange in the Liquid and Vapour Phases and Their Isomer Analyses by F NMR Spectroscopy*; Journal of Fluorine Chemistry, 43 (1989) pp. 155-175.
V. Petrov, C. Krespan and B. Smart, *Isomerization of Halopolyfluoroalkanes by the Action of Aluminum Chlorofluoride*, Journal of Fluorine Chemistry 89 (1998) pp. 125-130.
A. Feiring and A. Worm, *Introduction to Fluorinated Polymers, Part 1 and Part 2*, Division of Fluorine Chemistry—ACS, undated.
Milos Hudlicky, *Chemistry of Organic Fluorine Compounds*, 2$^{nd}$ (Revision Edition), 1992, pp. 728-729.
Billmeyer, Fred W., Jr., *Textbook of Polymer Science*, 1984, pp. 398-399.
US03/41851 Jun. 2004, PCT-Int'l Search Rpt.
US03/41851 Aug. 2006, PCT-IPER.

* cited by examiner

Primary Examiner—Sikarl A. Witherspoon
(74) Attorney, Agent, or Firm—Wells St. John P.S.

(57) ABSTRACT

Methods and materials are disclosed for the recovery of valuable hydrofluorocarbons and subsequent conversion to environmentally inert compounds. More specifically methods and materials are provided for recovering hydrofluorocarbons such as HFC-227, HFC-236, HFC-245, HFC-125, HFC-134, HFC-143, HFC-152, HFC-32, HFC-23 and their respective isomers. Processes are provided for converting hydrofluorocarbons such as these to fluoromonomer precursors such as CFC-217, CFC-216, CFC-215, CFC-115, CFC-114, CFC-113, CFC-112, HCFC-22, CFC-12, CFC-13 and their respective isomers. Materials, methods and schemes are provided for the conversion of these fluoromonomer precursors to fluoromonomers such as HFP, PFP, TFP, TFE, and VDF.

43 Claims, No Drawings

MATERIALS AND METHODS FOR THE CONVERSION OF HYDROFLUOROCARBONS

BACKGROUND OF THE INVENTION

In recent years, the use of hydrofluorocarbons has proliferated throughout the world as replacements and/or alternatives to the use of halon chemicals. Millions of metric tons of hydrofluorocarbons are created each year and distributed throughout the world for eventual use as refrigerants, extinguishants, sterilants, solvents, propellants and blowing agents.

As various contained hydrofluorocarbon uses, such as refrigerant use, and fire extinguishant use, may be decommissioned, a need exists for the conversion of hydrofluoro carbons to relatively inert fluorine containing compounds.

The present invention provides materials and methods for the conversion of hydrofluorocarbons to valuable fluorine containing precursors or compounds that may be transformed into benign fluorine containing compounds.

SUMMARY OF THE INVENTION

One embodiment of the present invention provides methods and materials for the conversion of hydrofluorocarbons to fluoromonomer precursors by replacing one or more hydrogen atoms of a hydrofluorocarbon with a halogen in the presence of halogenating agent. In another embodiment, the present invention incorporates a solid substrate to perform the conversion. In a specific embodiment, methods are provided for the conversion of 2H-heptafluoropropane (HFC-227ea, $CF_3CFHCF_3$) to the fluoromonomer precursor chloroheptafluoropropane (CFC-217ba, $CF_3CClFCF_3$) in the presence of activated carbon and chlorine. Embodiments of these conversions include conversions at temperatures between about 150° C. and about 400° C. or between about 275° C. and about 350° C. The process can also be carried out at less than about 24.0 $kg/cm^2$, or between about 6.66 $kg/cm^2$ and about 8.06 $kg/cm^2$. Fluoromonomer precursors such as CFC-217ba can subsequently be converted to fluoromonomers such as hexafluoropropene (HFP, $C_3F_6$) by dehalogenation.

Other embodiments of the present invention include the conversion of hexafluoropropane (HFC-236, $C_3F_6H_2$) to the fluoromonomer precursor dichlorohexafluoropropane (CFC-216, $C_3Cl_2F_6$) with subsequent conversion to the fluoromonomer pentafluoropropene (PFP, $C_3F_5H$) by dehalogenation. In another embodiment, methods are provided for the conversion of pentafluoropropane (HFC-245, $C_3F_5H_3$) to the fluoromonomer precursor trichloropentafluoropropane (CFC-215, $C_3Cl_3F_5$) with subsequent conversion to PFP by dehalogenation.

In another embodiment of the present invention, pentafluoroethane (HFC-125, $C_2F_5H$) is converted to the fluoromonomer precursor chloropentafluoroethane (CFC-115, $C_2ClF_5$) with subsequent conversion to the fluoromonomer tetrafluoroethene (TFE, $C_2F_4$) by dehalogenation. In another embodiment of ethane conversion, tetrafluoroethane (HFC-134, $C_2F_4H_2$) is converted to the fluoromonomer precursor dichlorotetrafluoroethane (CFC-114, $C_2Cl_2F_4$) which can be subsequently converted to TFE by dehalogenation.

Other embodiments of hydrofluoroethane conversion provide for the conversion of trifluoroethane (HFC-143, $C_2F_3H_3$) to trichlorotrifluoroethane (CFC-113, $C_2Cl_3F_3$) with subsequent conversion to difluoroethene (VDF, $C_2F_2H_2$) and the conversion of difluoroethane (HFC-152, $C_2F_2H_4$) to tetrachlorodifluoroethane (CFC-112, $C_2Cl_4F_2$) with subsequent conversion to VDF.

In still another embodiment, fluoromethanes are converted to fluoromonomer precursors which are subsequently converted to fluoromonomers such as trifluoropropene (TFP, $C_3F_3H_3$) by addition and subsequent reaction or to TFE by pyrolysis, depending on the conversion. In one embodiment, difluoromethane (HFC-32, $CF_2H_2$) is converted to the fluoromonomer precursor dichlorodifluoromethane (CFC-12, $CCl_2F_2$). Ethylene can then be added to this precursor to form the fluoroadduct dichlorodifluoropropane, which can subsequently be converted to TFP.

In another embodiment trifluoromethane (HFC-23, $CF_3H$) is converted to the fluoromonomer precursor chlorotrifluoromethane (CFC-13, $CClF_3$), which can be converted to the fluoroadduct chlorotrifluoropropane that can be converted to TFP.

In other embodiments, the hydrofluorocarbon compounds can be partially chlorinated to produce hydrochlorofluorocarbons that can be pyrolyzed to form fluoromonomers such as TFE. In one embodiment, HFC-32 is converted to the fluoromonomer precursor chlorodifluoromethane (HFC-22, $CClF_2H$) which can be pyrolyzed to form TFE.

DESCRIPTION OF THE INVENTION

For the purposes of promoting an understanding of the principles of the invention, reference will now be made to the embodiments illustrated in the examples and specific language will be used to describe the same. It will nevertheless be understood that no limitation of the scope of the invention is thereby intended. The invention includes any alterations and further modifications in the exemplified devices and described methods and further applications of the principles of the invention which would normally occur to one skilled in the art to which the invention relates.

The present invention provides materials and methods for the conversion of hydrofluorocarbons to relatively environmentally inert compounds. One embodiment of the present invention provides processes for converting hydrofluorocarbons to fluoromonomer precursors. Certain aspects of this embodiment include the conversion of hydrofluorocarbons such as HFC-227, HFC-236, HFC-245, HFC-125, HFC-134, HFC-143, HFC-152, HFC-32, HFC-23 and their respective isomers. These compounds can be converted to fluoromonomer precursors such as CFC-217, CFC-216, CFC-215, CFC-115, CFC-114, CFC-113, CFC-112, HCFC-22, CFC-12, CFC-13 and their respective isomers. Materials, methods and schemes are provided for the conversion of these fluoromonomer precursors to fluoromonomers such as HFP, PFP, TFP, TFE, and VDF. These fluoromonomers can be subsequently polymerized to inert fluoropolymers.

The hydrofluorocarbons contemplated for conversion by the present invention include, but are not limited to the hydrofluorocarbons mentioned previously and those hydrofluorocarbons having substantially the same amount of carbon atoms. More specifically, those compounds containing only hydrogen, carbon and fluorine, and blends of hydrofluorocarbons such as the common refrigerant blend of HFC-32 and HFC-125 are candidates for conversion according to the present invention. It is believed that the methodologies described herein allow for the conversion of these compounds and blends to their respective fluoromonomer precursors. For example, the HFC-125/HFC-32 blend may be converted, according to the present invention, to the fluoromonomer TFE.

The reactions described herein may be performed utilizing conventional gas-phase organic reaction procedures, product isolation and, if desired, materials can be recycled prior to the initial reaction which converts hydrofluorocarbons to fluoromonomer precursors. It may be desirable to utilize separation technologies such as fractional distillation, partial condensation, or heterogeneous liquid/liquid phase separation to isolate relatively pure hydrofluorocarbon from crude mixtures or blends. It is contemplated not only to have a separate recovery system for each reaction as is conventional, but in the case of the present reactions to combine the product streams for product isolation.

In one specific embodiment HFC-227 is converted to the fluoromonomer precursor HFC-217 which can subsequently be converted to HFP, a useful fluoromonomer. In one embodiment, the conversion of HFC-227 to HFC-217 is performed in the presence of the halogenating agent chlorine. As described herein, other hydrofluorocarbons that are suitable for conversion include HFC-236, HFC-245, HFC-125, HFC-134, HFC-143, HFC-152, HFC-32, HFC-23 and their respective isomers. These hydrofluorocarbons share the common characteristic of containing carbon, hydrogen and fluorine. To name a few applications, these compounds are typically used in industry as extinguishants, propellants, blowing agents, refrigerants, solvents and sterilants. The compounds may be acquired as blends with other compounds and, when possible, the hydrofluorocarbon can be separated prior to or subsequent the reaction with a halogen.

The present invention contemplates the use of halogenating agents when preparing the fluoromonomer precursors. Embodiments of the present invention may utilize halogenating agents such as chlorine, bromine, or iodine. These halogenating agents are conventionally provided in their diatomic form; $Cl_2$, $Br_2$ or $I_2$, but may also be provided as their hydrogenates; HCl, HBr or HI. These compounds are commercially available at purities of 99.9% or higher. Because of the corrosive nature of these compounds, the impurity amount, particularly the amount of water present in the reactants, is normally be kept to a minimum.

Many reactors are suitable for combining the hydrofluorocarbon and the halogen. Examples of these include Inconel™ and Monel™ brand alloy reactors and vitreous or glass lined reactors. Other halogenating agents include 1,3-dichloro-5,5-dimethylhydantoin, N-chlorosuccinimide, sulfuryl chloride and sodium hypochlorite. It is preferred that the reactors be resistant to the corrosive nature of the reactants, particularly the halogenating agents, and provide sufficient space to accommodate solid substrates when utilized. The present invention contemplates many techniques for heating the reactor; including heat tape, oil bath, steam, heat transfer fluids or ceramic heaters. Embodiments of these conversions include conversions at temperatures between about 150° C. and about 400° C. or between about 275° C. and about 350° C.

In another embodiment the present invention provides for the conversion of the hydrofluorocarbon in the presence of a solid substrate. This solid substrate includes both what is traditionally referred to as catalyst and what is traditionally referred to as a catalyst support. It is contemplated that the catalyst and catalyst support may be utilized separately or in combination.

The solid substrate of the present invention include but are not limited to activated carbon, iron, copper, aluminum, clay or metal oxides. These solid substrates may be used separately or as mixtures. In one particular embodiment of the present invention, Takeda™ brand $ZnCl_2$ activated carbon is utilized as the solid substrate.

Solid substrates useful with this reaction may be prepared in a myriad of ways. It is generally accepted that before contact with the reactants, the solid substrate should be heated and dried by passing a stream of inert gas, typically nitrogen through the reactor for a sufficient time to ensure activation and residual water removal. Once activated or purged, the reactor may be sealed from the atmosphere prior to providing the reactants. During the reaction, the pressure within the reactor may be maintained at approximately atmospheric pressure. Processes according to the present invention can also be carried out at less than about 24.0 $kg/cm^2$, or between about 6.66 $kg/cm^2$ and about 8.06 $kg/cm^2$.

Depending on the hydrofluorocarbon selected for conversion, the reactants may be provided to the reactor with pumps suitable for transferring liquids or gases. Example liquid pumps include peristaltic, syringe, rotary, centrifugal and positive displacement pumps. If a gas, the reactants may be provided to the reactor from a pressurized cylinder and regulated through a flowmeter or mass flow controller. Vacuum pumps may also be utilized to decrease pressure allowing for additional gas reactant addition. Processes according to the present invention can utilize pumps and flowmeters to provide reactants at specific mole ratios. According to one embodiment the mole ratio of halogenating agent to hydrofluorocarbon is 0.16 to 22. The mole ratio of the reactants will increase as the level of halogenation required increases. Corrosive resistant piping or tubing proves beneficial when providing reactants to the reactor.

Crude products obtained from the reactor can be purified by subsequent processes to allow for ease of analysis and increased efficiency of subsequent reactions. The present invention contemplates a spectra of subsequent product purification processes depending on the level of purity desired ranging from the absence of purification to multiple step purifications. Typically, the products of reactions contain by-products such as water, acids, unreacted halogens and/or organic compounds having lower or higher boiling points than the desired fluoromonomer precursors products.

It is generally accepted that the products can be scrubbed of acids such as HCl, HBr, HF, or HI by passing the products through a basic solution. These solutions include 5% (wt./wt.) to 10% (wt./wt.) solutions of potassium hydroxide or other acceptable bases. After scrubbing, the products can be dried of excess water by exposing the product to Drierite™ brand $CaSO_4$, $CaCl_2$, molecular sieve or other suitable drying techniques. Examples 1 and 2 below demonstrate the present invention for the conversion of HFC-227ea to the fluoromonomer precursor HFC-217ba.

Products were determined utilizing a Hewlett Packard 5890 Series II gas chromatograph equipped with a flame ionization detector and a plot fused silica 30 m×0.32 mm ID coated silicaplot™ gas chromatography column. The results are reported as percentages of total responses, or area percent. Tables 1 and 2 below demonstrate the conversion of HFC-227 in the presence of a solid support.

TABLE 1

Flowmeter Determined Reactant Amounts

| Run # | Temp (° C.) | Contact Time(s) | Cl$_2$:HFC-227 mole ratio | Conversion to CFC-217 | Selectivity to CFC-217ba | 227ca (ppm) | 217ca (ppm) |
|---|---|---|---|---|---|---|---|
| 1 | 200 | 12.6 | 1.73 | 0.7% | 81.5% | | |
| 2 | 250 | 13.3 | 2.02 | 24.5% | 98.9% | 628 | 219 |
| 3 | 300 | 12.8 | 1.83 | 54.5% | 98.9% | 640 | 223 |
| 4 | 325 | 11.9 | 1.50 | 48.2% | 96.8% | 744 | 217 |
| 5 | 325 | 21.9 | 2.76 | 98.9% | 97.9% | n/d | 767 |
| 6 | 350 | 13.2 | 2.0 | 65.5% | 96.2% | 548 | 281 |
| 7 | 325 | 21.2 | 2.38 | 91.7% | 97.9% | | |
| 8 | 325 | 22.3 | 2.88 | 98.1% | 98.3% | 63 | 751 |
| 9 | 200 | 24.7 | 2.0 | 30.2% | 90.9% | 1152 | 335 |
| 10 | 200 | 38.5 | 0.16 | 3.2% | 71.2% | 981 | 55 |
| 11 | 200 | 24.1 | 0.34 | 2.2% | 77.8% | 880 | n/d |
| 12 | 300 | 21.8 | 0.54 | 44.8% | 96.5% | 701 | 211 |
| 13 | 325 | 36.1 | 1.2 | 95.9% | 98.9% | 157 | 1253 | n/d = none detected

TABLE 2

HFC-227 (Spiked* with HFC-227ca Isomer)

| Run # | Temp (C) | Contact Time(s) | Cl$_2$:HFC-227 mole ratio | Conversion to CFC-217 | Selectivity to CFC-217ba | 227ca (ppm) | 217ca (ppm) |
|---|---|---|---|---|---|---|---|
| 1 | 300 | 16.3 | 0.17 | 18.3% | 96.8% | 1255 | 113 |
| 2 | 300 | 15.8 | 0.35 | 46.8% | 98.6% | 899 | 414 |
| 3 | 300 | 14.6 | 0.32 | 55.6% | 98.5% | 829 | 531 |
| 4 | 300 | 26.9 | 0.80 | 79.2% | 98.7% | 341 | 930 |

*1415 ppm 227ca in Reactant

EXAMPLE 1

HFC-227→HFC-217

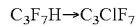

A 34 cubic centimeter Inconel™ reactor tube, equipped with a ceramic fiber heater, was packed with Takeda™ brand activated carbon. The activated carbon and reactor were purged with nitrogen between 150° C. and 200° C. The reactor was connected to tubing providing chlorine and the hydrofluorocarbon heptafluoropropane (HFC-227, containing 839 ppm 227ca and the remainder HFC-227ea). The flow of the chlorine and HFC-227 were controlled with gas flowmeters. Tables 1 and 2 below indicate the reaction parameters as well as the results. Fluoromonomer precursor chloroheptafluoropropane (CFC-217) exiting the reactor was first passed through a 10% (wt./wt.) KOH solution and then dried over $CaSO_4$ before being captured for subsequent gas chromatography analysis.

EXAMPLE 2

HFC-227→HFC-217

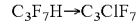

According to another embodiment of the present invention, a 34 cubic centimeter Inconel™ reactor tube is equipped with a ceramic fiber heater. The reactor is purged with nitrogen between 150° C. and 200° C. The reactor is connected to tubing providing chlorine and the hydrofluorocarbon heptafluoropropane (HFC-227). The flow of the chlorine and HFC-227 is controlled with gas flowmeters. Table 3 below indicates the suggested reaction parameters as well as the expected results. Fluoromonomer precursor chloroheptafluoropropane (CFC-217) exiting the reactor is first passed through a 10% (wt./wt.) KOH solution and then dried over $CaSO_4$, before being captured for subsequent gas chromatography analysis.

Products are determined utilizing a Hewlett Packard 5890 Series II as chromatograph equipped with a flame ionization detector and silicaplot™ fused silica 30 m×0.32 mm ID coated gas chromatograph column.

TABLE 3

HFC-227→CFC-217 (open tube)

| Run # | Temp (° C.) | Contact Time(s) | Cl$_2$:HFC-227 mole ratio | Conversion to CFC-217 | Selectivity to CFC-217ba |
|---|---|---|---|---|---|
| A | ~325 | ~20 | ~2 | Acceptable | Acceptable |

In accordance with still another embodiment of the present invention, the fluoromonomer precursor of the present invention is contacted with H$_2$ and a catalyst to form a fluoromonomer. In one embodiment the fluoromonomer precursors are the reaction product of the conversion of HFC-227, which include CFC-217. Accordingly, using the general gas phase reaction schemes described herein or methods consistent with those described in U.S. Pat. No. 5,057,634 to Webster, herein incorporated by reference, the fluoromonomer precursors and hydrogen are contacted with a catalyst in a reactor at sufficient temperature to produce fluoromonomer. In one embodiment the fluoromonomer product of HFC-217 includes HFP.

To prepare the fluoromonomer, a slight molar excess of H$_2$ can be used if desirable but is not necessary. The H$_2$:fluoromonomer precursor molar ratio can be in the range of about 0.2:1 to about 10:1, optimally about 1.2:1.

The fluoromonomer can be prepared in a fixed bed reactor containing a suitable catalyst, such as palladium on a refractory oxide support, or alumina or other suitable supports. The reactor can be operated at a temperature of about 30° C. to about 500° C., or at about 300° C.

The pressure in the reactor may be in the range of about 1.0 kg/cm$^2$ to about 7.4 kg/cm$^2$, and preferably about 7.0 kg/cm$^2$. The reaction is largely insensitive to pressure in the range of 1.0–7.9 kg/cm$^2$, however, reaction selectivity is slightly favored by lower pressures. Contact time in the reactor should be in the range of about 6 seconds to about 90 seconds, and optimally about 10 to about 30 seconds.

As those skilled in the art appreciate, there is a relationship between catalyst activity, temperature, pressure, and contact time such that more active catalyst and higher pressure permit operation at lower temperature and shorter contact time.

Catalysts appropriate for converting the fluoromonomer precursor to the fluoromonomer are common hydrogenation catalysts such as Co, Ni, Cr, Cu or combinations thereof, optionally promoted with compounds of Mo, V, W, Ag, Fe, K, Ba or combinations thereof. While not critical to performance, specificity of the conversion to the fluoromonomer increases when utilizing a supported catalyst. Useful supports include carbon, metal fluorides, alumina and titanium.

The addition of water during this reaction allows the catalyst to perform for extended periods of time with no apparent loss of activity. The chemistry is not particularly sensitive to the amount of water present above a minimum of 0.2%. It has been determined that this process enhancement will test favorably with various catalysts. The additional water is from about 0.04 to about 12 percent by weight of the fluoromonomer precursor, or about 0.8 percent by weight of the fluoromonomer precursor. Example 3 below demonstrates the expected dehalogenation of the fluoromonomer precursor CFC-217. Example 4 demonstrates the expected conversion of HFC-236 to PFP.

EXAMPLE 3

HFC-217→HFP

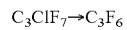
$C_3ClF_7 \rightarrow C_3F_6$

A 34 cubic centimeter Inconel™ reactor tube containing 10% (wt./wt.) NiCl$_2$ on activated carbon was heated by an electric heater and the fluoromonomer precursor CFC-217ba and H$_2$ combined according to the parameters indicated in Table 4 below. The resulting crude organic gas product is then washed with water to remove acids and analyzed by gas chromatography. Table 4 below demonstrates the results of this dehalogenation.

TABLE 4

CFC-217→HFP

| Run # | Contact Time(s) | Temp. ° C. | H$_2$:CFC-217 mole ratio | % HFP |
|---|---|---|---|---|
| 1 | 11.0 | 250 | 8.0 | 21.6 |
| 2 | 11.0 | 300 | 12.0 | 92.3 |
| 3 | 10.9 | 300 | 9.0 | 92.3 |
| 4 | 5.8 | 300 | 17.8 | 23.2 |

EXAMPLE 4

HFC-236→PFP

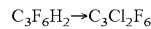
$C_3F_6H_2 \rightarrow C_3Cl_2F_6$

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chlorine and the hydrofluorocarbon hexafluoropropane (HFC-236). The flow of the chlorine and hexafluoropropane are controlled with gas flowmeters. The temperature of the reactor is brought to approximately 325° C. and the flow of the chlorine and HFC-236 is set to the flow rate that allows for a mole ratio of approximately 2. Fluoromonomer precursor dichlorohexafluoropropane (CFC-216) exiting the reactor is first passed through a 10% KOH solution and then dried over CaSO$_4$ before being captured for subsequent conversion to PFP.

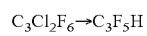
$C_3Cl_2F_6 \rightarrow C_3F_5H$

A 34 cubic centimeter Inconel™ reactor tube was heated by an electric heater and the fluoromonomer precursor CFC-216 and H$_2$ combined therein according to the parameters indicated in Table 5 below. The resulting crude organic product was then washed with water to remove acids leaving the fluoromonomer PFP.

Products are determined utilizing a Hewlett Packard 5890 Series II gas chromatograph equipped with a flame ionization detector and a plot fused silica 30 m×0.32 mm ID coating silicaplot™ column. The results are reported as percentages of total responses or area percent. Table 5 below demonstrates the expected results of this conversion.

TABLE 5

CFC-216→PFP

| Run # | Contact Time(s) | Temp ° C. | H$_2$:CFC-216 mole ratio | % PFP |
|---|---|---|---|---|
| 1 | 8.6 | 300 | 9.9 | 70.6 |
| 2 | 7.7 | 325 | 9.9 | 77.5 |
| 3 | 7.2 | 350 | 10.2 | 81.9 |
| 4 | 7.2 | 375 | 10.2 | 84.0 |
| 5 | 8.0 | 380 | 8.3 | 86.8 |
| 6 | 10.8 | 450 | 6.8 | 61.4 |

EXAMPLE 5

HFC-245→PFP $C_3F_5H_3 \rightarrow C_3Cl_3F_5$

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chloride and the hydrofluorocarbon pentafluoropropane (HFC-245). The flow of the chlorine and HFC-245 are controlled with gas flowmeters. The temperature of the reactor is brought to approximately 325° C. and the flow of the chlorine and HFC-245 is set to the flow rate that allows for a mole ratio of approximately 3. Fluoromonomer precursor trichloropentafluoropropane (CFC-215) exiting the reactor is first passed through a 10% KOH solution and then dried over CaSO$_4$ before being captured for subsequent conversion to PFP.

$C_3Cl_3F_5 \rightarrow C_3F_5H$

A 34 cubic centimeter Inconel™ reactor tube was heated by an electric heater to combine the fluoromonomer precursor CFC-215 and H$_2$ according to the parameters indicated in Table 6. The resulting crude organic product was then washed with water to remove acids leaving the fluoromonomer PFP.

Products are determined utilizing a Hewlett Packard 5890 Series II gas chromatograph equipped with a flame ionization detector and a plot fused silica 30 m×0.32 mm ID coating silicaplot™ column. Table 6 below demonstrates the results of this conversion.

TABLE 6

CFC-215→PFP

| Run # | Contact Time(s) | Temp. ° C. | H$_2$:CFC-215 mole ratio | % PFP |
|---|---|---|---|---|
| 1 | 30.4 | 100 | 17.8 | 52.7 |
| 2 | 30.4 | 135 | 17.8 | 62.0 |

EXAMPLE 6

HFC-125→TFE $C_2F_5H \rightarrow C_2ClF_5$

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chlorine and the hydrofluorocarbon pentafluoroethane (HFC-125). The flow of the chlorine and HFC-125 are controlled with gas flowmeters. The temperature of the reactor is brought to approximately 325° C. and the flow of the chlorine and HFC-125 is set to the flow rate that allows for a mole ratio of approximately 1. Fluoromonomer precursor chloropentafluoroethane (CFC-115) exiting the reactor is first passed through a 10% KOH solution and then dried over CaSO$_4$ before being captured for subsequent conversion to TFE.

$C_2ClF_5 \rightarrow C_2F_4$

A 34 cubic centimeter Inconel™ reactor tube is packed with a NiCl$_2$ catalyst and heated by an electric heater to combine the fluoromonomer precursor CFC-215 and H$_2$ in a ratio of about 2 and a temperature of about 300° C. The resulting crude organic gas product is then washed with water to remove acids leaving the fluoromonomer TFE.

Products are determined utilizing a Hewlett Packard 5890 Series II gas chromatograph equipped with a flame ionization detector and a plot fused silica 30 m×0.32 mm ID coating silicaplot™ column. Table 7 below demonstrates the expected results of this conversion.

TABLE 7

CFC-125→TFE

| | | HFC-125→HFC-115 | | CFC-115→TFE | | |
|---|---|---|---|---|---|---|
| Run # | Temp. ° C. | Cl$_2$:HFC-125 Ratio | Conversion to CFC-115 | H$_2$:CFC-115 Ratio | Temp. ° C. | Conversion to TFE |
| 1 | ~300 | ~1 | Acceptable | ~2 | 300 | Acceptable |

EXAMPLE 7

HFC-134→TFE

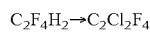

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chlorine and the hydrofluorocarbon tetrafluoroethane (HFC-134). The flow of the chlorine and HFC-134 are controlled with gas flowmeters. The reaction parameters are those indicated in Table 8 below. Fluoromonomer precursor dichlorotetrafluoroethane (CFC-114) exiting the reactor is first passed through a 10% KOH solution and then dried over CaSO$_4$ before being captured for subsequent conversion to TFE.

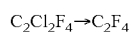

A 34 cubic centimeter Inconel™ reactor tube can be packed with a supported Pd/Cu catalyst and heated by an electric heater to combine the CFC-114 and H$_2$ in a ratio of about 8 and a temperature of about 350° C. The resulting crude organic gas product is then washed with water to remove acids leaving the fluoromonomer TFE.

Products are determined utilizing a Hewlett Packard 5890 Series II gas chromatograph equipped with a flame ionization detector and a plot fused silica 30 m×0.32 mm ID coating silicaplot™ column. Table 8 below demonstrates the expected results of this conversion.

HFC-143→VDF

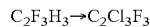

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chlorine and the hydrofluorocarbon trifluoroethane (HFC-143). The flow of the chlorine and HFC-143 are controlled at a mole ratio of about 22 and the reaction is maintained at a temperature of about 300° C. Fluoromonomer precursor trichlorotrifluoroethane (CFC-113) exiting the reactor is first passed through a 10% KOH solution and then dried over CaSO$_4$ before being captured for subsequent conversion to difluoroethene (VDF).

A 34 cubic centimeter Inconel™ reactor tube can be packed with a supported Pd/Cu catalyst and heated by an electric heater to combine the CFC-113 and H$_2$ in a ratio of about 8 and a temperature of about 350° C. The resulting crude organic gas product is then washed with water to remove acids leaving the fluoromonomer VDF.

Products are determined utilizing a Hewlett Packard 5890 Series II gas chromatograph equipped with a flame ionization detector and a plot fused silica 30 m×0.32 mm ID coating silicaplot™ column. Table 9 below demonstrates the expected results of this conversion.

TABLE 8

HFC-134→TFE

| | | HFC-134→CFC-114 | | CFC-114→TFE | | |
|---|---|---|---|---|---|---|
| Run # | Temp. ° C. | Cl$_2$:HFC-134 Ratio | Conversion to CFC-114 | H$_2$:CFC-114 Ratio | Temp. ° C. | Conversion to TFE |
| 1 | ~300 | 22.0 | Acceptable | ~8.0 | ~350 | Acceptable |

EXAMPLE 8

TABLE 9

HFC-143→VDF

| | | HFC-143→CFC-113 | | CFC-113→VDF | | |
|---|---|---|---|---|---|---|
| Run # | Temp. ° C. | Cl$_2$:HFC-143 Ratio | Conversion to CFC-113 | H$_2$:CFC-113 Ratio | Temp. ° C. | Conversion to VDF |
| 1 | ~300 | ~22.0 | Acceptable | ~8.0 | ~350 | Acceptable |

EXAMPLE 9

HFC-152→VDF

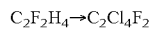

A 34 cubic centimeter Inconel™ reactor tube, equipped with a ceramic fiber heater, is packed with activated carbon. The activated carbon and reactor are purged with nitrogen between 150° C. and 200° C. The reactor is connected to tubing providing chlorine and the hydrofluorocarbon difluoroethane (HFC-152). The flow of the chlorine and HFC-152 are maintained at a mole ratio of about 22 and the reactor is maintained at a temperature of about 300° C. Fluoromonomer precursor tetrachlorodifluoroethane (CFC-112) exiting the reactor is first passed through a 10% KOH solution and then dried over CaSO₄ before being captured for subsequent conversion to difluoroethene (VDF).

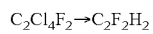

A 34 cubic centimeter Inconel™ reactor tube can be packed with a supported Pd/Cu catalyst and heated by an electric heater to combine the CFC-112 and $H_2$ in a ratio of about 8 and a temperature of about 350° C. The resulting crude organic gas product is then washed with water to remove acids leaving the fluoromonomer VDF.

Products are determined utilizing a Hewlett Packard 5890 Series II gas chromatograph equipped with a flame ionization detector and a plot fused silica 30 m×0.32 mm ID coating silicaplot™ column. Table 10 below demonstrates the expected results of this conversion.

TABLE 10

| | HFC-152→VDF | | | | | |
|---|---|---|---|---|---|---|
| | HFC-152→CFC-112 | | | CFC-112→VDF | | |
| Run # | Temp. ° C. | Cl₂:HFC-152 Ratio | Conversion to CFC-112 | H₂:CFC-112 Ratio | Temp. ° C. | Conversion to VDF |
| 1 | ~300 | ~22.0 | Acceptable | ~8.0 | ~350 | Acceptable |

According to another embodiment of the present invention, methyl hydrofluorocarbons may be recovered and converted to fluoromonomers by converting the methyl hydrofluorocarbon to a fluoromonomer precursor and then adding additional carbon chain length with an olefin such as ethylene before subsequent conversion to a fluoromonomer.

As described herein, methyl hydrofluorocarbons such as difluoromethane (HFC-32) or trifluoromethane (HFC-23) are converted to useful fluoromonomer precursors such as dichlorodifluoromethane (CFC-12) and chlorotrifluoromethane (CFC-13). To provide inert fluoromonomers, these compounds are added to relatively inexpensive compounds such as ethylene before being fluorinated or dehalogenated to fluoromonomers such as TFP.

The addition can be performed in the liquid phase by combining the fluoromonomer precursor with the olefin in the presence of a catalyst to form a fluoroadduct or alternatively the addition can be performed in the presence of a stabilizing agent such as tributyl phosphate.

In one embodiment, the fluoromonomers precursor is CFC-12, the alkene is ethylene, and the catalyst is a mixture of iron and tributyl phosphate. It has been determined that other stabilizing agents containing phosphorous could be used. In a particular embodiment, the ratio of fluoromonomer precursor to alkene is about 1.07:1, the temperature is about 105° C. and the pressure is about 1.4–2.1 kg/cm².

CFC-12 and ethylene in the presence of a catalyst react to form dichlorodifluoropropane. This dichlorodifluoropropane can subsequently be halogenated in the presence of HF to form the fluoromonomer trifluoropropene (TFP).

According to an alternative embodiment of the present invention, HFC-32 is converted to the fluoromonomer precursor HCFC-22 which is traditionally converted to TFE by pyrolysis. Example 10 below demonstrates the conversion of HFC-32 to both TFP and TFE.

EXAMPLE 10

HFC-32→TFP and TFE

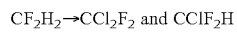

A 34 cubic centimeter Inconel™ reactor tube, equipped with a ceramic fiber heater, was, in one instance packed with Takeda™ brand activated carbon and in another left empty. The reactors were purged with nitrogen between 150° C. and 200° C. The reactors were connected to tubing providing chlorine and the hydrofluorocarbon difluoromethane (HFC-32). The flow of the chlorine and HFC-32 were controlled with gas flowmeters. The parameters of these reactions are indicated in Tables 11 and 12 below. Fluoromonomer precursors dichlorodifluoromethane (CFC-12) or chlorodifluoromethane (HCFC-22) exiting the reactor were first passed through a 10% KOH solution and then dried over CaSO₄ before being captured for subsequent transformation to the desired fluoromonomer. Table 11 below demonstrates the conversion of HFC-32 utilizing a catalyst at varying reagent mole ratios, contact times and temperatures. Table 12 demonstrates the conversion of HFC-32 in an empty reactor at varying reagent mole ratios, contact times and temperatures.

TABLE 11

HFC-32→CFC-22/CFC-12

| Run # | Temp. (° C.) | Contact time(s) | Mole Ratio (Cl$_2$:HFC-32) | Conv. % | Sel. HCFC-22% | Sel. CFC-12% | Total Sel. % |
|---|---|---|---|---|---|---|---|
| 1 | 200 | 12.3 | 1.22 | 30.89 | 80.69 | 17.51 | 98.2 |
| 2 | 250 | 6.96 | 0.76 | 74.01 | 56.76 | 40.69 | 97.45 |
| 3 | 250 | 8.35 | 3.44 | 57.72 | 69.75 | 21.95 | 91.7 |
| 4 | 300 | 7.78 | 3.83 | 96.64 | 32.44 | 65.8 | 98.24 |
| 5 | 300 | 11.82 | 1.11 | 61.96 | 52.59 | 41.2 | 93.79 |
| 6 | 300 | 11.82 | 1.11 | 61.96 | 52.59 | 41.2 | 93.79 |
| 7 | 300 | 19.22 | 2.27 | 97.78 | 23.18 | 74.37 | 97.55 |
| 8 | 300 | 4.67 | 1.22 | 61.65 | 44.64 | 49.1 | 93.74 |
| 9 | 350 | 4.97 | 0.87 | 45.56 | 45.99 | 43.24 | 89.23 |
| 10 | 200 | 18.19 | 0.86 | 5.55 | 77.01 | 4.58 | 81.59 |

TABLE 12

HFC-32→CFC-22/CFC-12 (open tube)

| Run # | Temp. (° C.) | Contact time(s) | Mole Ratio (Cl$_2$:HFC-32) | Conv. % | Sel. HCFC-2% | Sel. CFC-12% |
|---|---|---|---|---|---|---|
| 1 | 250 | 8.85 | 1.01 | 0.5 | 56 | 2 |
| 2 | 300 | 8.67 | 0.93 | 1.92 | 86.14 | 0.62 |
| 3 | 350 | 10.65 | 1.14 | 24.16 | 91.7 | 2.55 |
| 4 | 400 | 11.65 | 1.51 | 91.84 | 15.72 | 64.04 |
| 5 | 400 | 8.47 | 0.74 | 51.74 | 21.58 | 46.46 |
| 6 | 350 | 19.13 | 0.76 | 27.13 | 38.06 | 0.66 |
| 7 | 350 | 5.51 | 2.28 | 17.96 | 60.11 | 0.71 |
| 8 | 350 | 15.54 | 0.28 | 27.56 | 4.18 | 0.06 |

$CCl_2F_2 + C_2H_4 \rightarrow C_3Cl_2F_2H_4$

To perform the addition, a 1 inch I.D. by 24 inch long continuous reactor is equipped with a sight glass, circulation pump and pressure control valve. Sufficient iron wire is added to the reactor followed by the addition of the fluoromonomer precursor dichlorodifluoromethane (CFC-12), containing 3% by weight tributyl phosphate. The CFC-12 is added to the reactor in an amount sufficient to fill the reactor to 60% of its total volume. The reactor is then heated to approximately 105° C. and ethylene is added to the reactor until the fluoroadduct dichlorodifluoropropane concentration reaches a concentration of 66% by weight. A mixture of 3% tributyl phosphate/CFC-12 and ethylene is then continuously fed into the reactor in a mole ratio of 1.07:1. Reaction pressure is controlled at approximately 7.0 kg/cm$^2$ and the product was removed by liquid level control.

$C_3Cl_2F_2H_4 \rightarrow C_3F_3H_3$

A 34 cubic centimeter Inconel™ reactor tube can be heated by an electric heater to combine the HF and fluoroadduct dichlorodifluoropropane in a ratio of about 2 and a temperature of about 350° C. The resulting crude organic gas product is then washed with water to remove acids leaving the fluoromonomer TFP.

Products are determined utilizing a Hewlett Packard 5890 Series II gas chromatograph equipped with a flame ionization detector and a plot fused silica 30 m×0.32 mm ID coating silicaplot™ column. Table 13 below demonstrates the expected conversion of CFC-12 to TFP.

TABLE 13

CFC-12→TFP

| | CFC-12→Fluoroadduct | | | Fluoroadduct→TFP | | |
|---|---|---|---|---|---|---|
| Run # | Temp. ° C. | C$_2$H$_4$:CFC-12 Ratio | Conversion to Fluoroadduct | HF:Fluoroadduct Ratio | Temp. ° C. | Conversion to TFP |
| 1 | ~100 | ~1.0 | Acceptable | ~2.0 | ~350 | Acceptable |

$CClF_2H \rightarrow C_2F_4$

HCFC-22 is pyrolized at sufficient temperature to prepare TFE which is captured by cold trapping technique.

EXAMPLE 11

HFC-23→TFP $CF_3H \rightarrow CClF_3$

A 34 cubic centimeter Inconel™ reactor tube equipped with a ceramic fiber heater, is packed with Takeda™ brand activated carbon. The activated carbon and reactor are purged with nitrogen between 150° C. and 200° C. The reactor is connected to tubing providing chlorine and fluoromonomer precursor trifluoromethane (HFC-23). The flow of the chlorine and HFC-23 are maintained at a mole a ratio of about 3 and a reaction temperature of about 300° C. Fluoromonomer precursor chlorotrifluoromethane (CFC-13) exiting the reactor is first passed through a 10% KOH solution and then dried over CaSO$_4$ before being captured for subsequent conversion to a fluoroadduct. Table 14 below demonstrates the expected results for this conversion.

TABLE 14

HFC-23→CFC-13

| Run # | Temp. (° C.) | Contact time(s) | Mole Ratio (Cl$_2$:HFC-23) | CFC-13 Recovery |
|---|---|---|---|---|
| 1 | ~300 | 12.3 | ~3.0 | Acceptable |

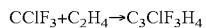

CFC-13 is combined with ethylene in a 1 inch I.D. by 24 inch long continuous reactor equipped with a sight glass, circulation pump and pressure control valve. Sufficient iron wire to catalyze the reaction is added to the reactor followed by the addition of CFC-13, containing 3% by weight tributyl phosphate. The CFC-13 is added to the reactor in an amount sufficient to fill the reactor to 60% of its total volume. The reactor is then heated to a sufficient temperature to facilitate the reactions, approximately 105° C. and ethylene is added to the reactor until the fluoroadduct chlorotrifluoropropane concentration reaches a concentration of 66% by weight. A mixture of 3% tributyl phosphate/CFC-13 and ethylene is then continuously fed into the reactor in a mole ratio of 1.07:1. Reaction pressure is controlled at approximately 7 kg/cm$^2$ and the product is removed by liquid level control.

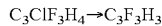

A 34 cubic centimeter Inconel™ reactor tube can be heated by an electric heater to combine the fluoroadduct chlorotrifluoropropane and H$_2$ in a ratio of about 2 and a temperature of about 350° C. The resulting crude organic gas product is then washed with water to remove acids leaving the fluoromonomer TFP.

Products are determined utilizing a Hewlett Packard 5890 Series II gas chromatograph equipped with a flame ionization detector and a plot fused silica 30 m×0.32 mm ID coating silicaplot™ column. Table 15 below demonstrates the expected results for this conversion.

TABLE 15

CFC-13→TFP

| | | CFC-13→Fluoroadduct | | Fluoroadduct→TFP | |
|---|---|---|---|---|---|
| Run # | Temp. ° C. | C$_2$H$_4$: CFC-13 Ratio | Conversion to Fluoroadduct | H$_2$: Fluoroadduct Ratio | Temp. ° C. | Conversion to TFP |
| 1 | ~100 | ~1.0 | Acceptable | ~2.0 | ~350 | Acceptable |

Fluoromonomers such as the HFP, PFP, TFP, VDF and TFE produced in the previous embodiments represent in many respects the backbone of fluoropolymers that demonstrate useful polymer properties. Within this family are found materials of high thermal stability and concurrent usefulness at high temperatures (in some cases combined with high crystalline melting points and high melt viscosity), and extreme toughness and flexibility at very low temperatures. Many of the fluoropolymers are almost totally insoluble and chemically inert, some have extremely low dielectric loss and high dielectric strength, and most have non-adhesive and low friction properties.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A process comprising replacing the hydrogen atom of C$_3$F$_7$H with a halogen in the presence of a halogenating agent and a catalyst to form a fluorocarbon compound comprising the halogen, wherein the replacing occurs in the absence of catalytic ultraviolet radiation.

2. The process of claim 1 wherein the replacing occurs within a reactor, a temperature within the reactor being between about 150° C. and about 400° C. during the replacing.

3. The process of claim 1 wherein the replacing occurs within a reactor, a temperature within the reactor being between about 275° C. and about 350° C. during the replacing.

4. The process of claim 1 wherein the replacing occurs within a reactor, a pressure within the reactor being less than about 24 kg/cm$^2$ during the replacing.

5. The process of claim 1 wherein the replacing occurs within a reactor, a pressure within the reactor being from about 6.66 kg/cm$^2$ to about 8.06 kg/cm$^2$ during the replacing.

6. The process of claim 1 wherein the replacing occurs within a reactor and the halogenating agent and the C$_3$F$_7$H are provided to the reactor at a mole ratio of halogenating agent to C$_3$F$_7$H from about 0.16 to about 22.

7. The process of claim 1 wherein the replacing occurs within a reactor and the halogenating agent and the C$_3$F$_7$H are provided to the reactor at a mole ratio of halogenating agent to C$_3$F$_7$H from about 1 to about 4.

8. The process of claim 1 wherein the hydrofluorocarbon comprises one or both of CF$_3$CHFCF$_3$ and CHF$_2$CF$_2$CF$_3$.

9. The process of claim 1 wherein the fluorocarbon compound comprises C$_3$ClF$_7$.

10. The process of claim 1 wherein the halogenating agent comprises one or more of bromine, chlorine, and iodine.

11. The process of claim 1 wherein the catalyst comprises a solid substrate.

12. The process of claim 11 wherein the solid substrate comprises one or more of activated carbon, Fe, Cu, Al, clay, and metal oxides.

13. The process of claim 11 wherein the solid substrate comprises activated carbon.

14. A process comprising replacing one or more hydrogen atoms of a hydrofluorocarbon with a halogen in the presence of a halogenating agent and a catalyst to form a fluorocarbon compound comprising the halogen, wherein the replacing occurs in the absence of catalytic ultraviolet radiation and further reacting the fluorocarbon compound to form a fluoromonomer.

15. The process of claim 14 further comprising preparing a fluoroadduct from the fluorocarbon compound.

16. The process of claim 1 wherein the replacing occurs within a reactor, the reactor configured to prevent exposure of the hydrofluorocarbon within the reactor to ultraviolet radiation during the replacing.

17. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, the converting comprising:
  replacing one or more hydrogen atoms of the hydrofluorocarbon with a halogen to form a fluorocarbon compound, wherein the fluorocarbon compound comprises the halogen;
  dehalogenating the fluorocarbon compound to form a fluoromonomer; and
  polymerizing the fluoromonomer to form the fluorinated compound.

18. The process of claim 17 wherein the replacing comprises exposing the hydrofluorocarbon to a halogenating agent to form the fluorocarbon compound.

19. The process of claim 18 wherein the halogenating agent comprises one or more of chlorine, bromine, and iodine.

20. The process of claim 17 wherein the dehalogenating comprises exposing the fluorocarbon compound to a dehalogenating agent to form the fluoromonomer.

21. The process of claim 20 wherein the dehalogenating agent comprises hydrogen.

22. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein the fluorinated compound comprises a fluoropolymer.

23. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CF_3CHFCF_3$; and
  the fluorinated compound comprises a fluoropolymer product of polymerized $CF_3CFCF_2$.

24. The process of claim 17 wherein:
  the saturated hydrofluorocarbon comprises $CF_3CHFCF_3$;
  the fluorocarbon compound comprises $CF_3CClFCF_3$;
  the fluoromonomer comprises $CF_3CFCF_2$; and
  the fluorinated compound comprises a fluoropolymer product of polymerized $CF_3CFCF_2$.

25. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CF_3CH_2CF_3$; and
  the fluorinated compound comprises a fluoropolymer product of polymerized $CF_3CHCF_2$.

26. The process of claim 17 wherein:
  the saturated hydrofluorocarbon comprises $CF_3CH_2CF_3$;
  the fluorocarbon compound comprises $CF_3CCl_2CF_3$;
  the fluoromonomer comprises $CF_3CHCF_2$; and
  the fluorinated compound comprises a fluoropolymer product of polymerized $CF_3CHCF_2$.

27. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CF_3CH_2CHF_2$; and
  the fluorinated compound comprises a fluoropolymer product of polymerized $CF_3CHCF_2$.

28. The process of claim 17 wherein:
  the saturated hydrofluorocarbon comprises $CF_3CH_2CHF_2$;
  the fluorocarbon compound comprises $CF_3CCl_2CClF_2$;
  the fluoromonomer comprises $CF_3CHCF_2$; and
  the fluorinated compound comprises a fluoropolymer product of polymerized $CF_3CHCF_2$.

29. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CF_3CF_2H$; and
  the fluorinated compound comprises a fluoropolymer product of polymerized $CF_2CF_2$.

30. The process of claim 17 wherein:
  the saturated hydrofluorocarbon comprises $CF_3CF_2H$;
  the fluorocarbon compound comprises $CF_3CF_2Cl$;
  the fluoromonomer comprises $CF_2CF_2$; and
  the fluorinated compound comprises a fluoropolymer product of polymerized $CF_2CF_2$.

31. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CF_2HCF_2H$; and
  the fluorinated compound comprises a fluoropolymer product of polymerized $CF_2CF_2$.

32. The process of claim 17 wherein:
  the saturated hydrofluorocarbon comprises $CF_2HCF_2H$;
  the fluorocarbon compound comprises $CF_2ClCF_2Cl$;
  the fluoromonomer comprises $CF_2CF_2$; and
  the fluorinated compound comprises a fluoropolymer product of polymerized $CF_2CF_2$.

33. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
  the saturated hydrofluorocarbon comprises $CHF_2CH_2F$; and
  the fluorinated compound comprises a fluoropolymer product of polymerized $CF_2CH_2$.

34. The process of claim 17 wherein:
  the saturated hydrofluorocarbon comprises $CHF_2CH_2F$;
  the fluorocarbon compound comprises $CClF_2CCl_2F$;
  the fluoromonomer comprises $CF_2CH_2$; and
  the fluorinated compound comprises a fluoropolymer product of polymerized $CF_2CH_2$.

35. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
the saturated hydrofluorocarbon comprises $CH_2FCH_2F$; and
the fluorinated compound comprises a fluoropolymer product of polymerized $CF_2CH_2$.

36. The process of claim 17 wherein:
the saturated hydrofluorocarbon comprises $CH_2FCH_2F$;
the fluorocarbon compound comprises $CCl_2FCCl_2F$;
the fluoromonomer comprises $CF_2CH_2$; and
the fluorinated compound comprises a fluoropolymer product of polymerized $CF_2CH_2$.

37. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein:
the saturated hydrofluorocarbon comprises $CF_2CH_2$; and
the fluorinated compound comprises a fluoropolymer product of polymerized $CF_3CHCH_2$.

38. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein the converting comprises:
replacing one or more hydrogen atoms of the hydrofluorocarbon with a halogen to form a fluorocarbon compound, wherein the fluorocarbon compound comprises the halogen;
preparing a fluoroadduct from the fluorocarbon compound;
dehalogenating the fluoroadduct to form a fluoromonomer; and
polymerizing the fluoromonomer to form the fluorinated compound.

39. The process of claim 38 wherein:
the saturated hydrofluorocarbon comprises $CF_2H_2$;
the fluorocarbon compound comprises $CF_2Cl_2$;
the fluoroadduct comprises $C_3Cl_2F_2H_4$;
the fluoromonomer comprises $CF_3CHCH_2$; and
the fluorinated compound comprises a fluoropolymer product of polymerized $CF_3CHCH_2$.

40. The process of claim 38 wherein:
the saturated hydrofluorocarbon comprises $CF_3H$;
the fluorocarbon compound comprises $CF_3Cl$;
the fluoroadduct comprises $C_3ClF_3H_4$;
the fluoromonomer comprises $CF_3CHCH_2$; and
the fluorinated compound comprises a fluoropolymer product of polymerized $CF_3CHCH_2$.

41. The process of claim 17 wherein:
the saturated hydrofluorocarbon comprises $CF_2H_2$;
the fluorocarbon compound comprises $CClF_2H$;
the fluoromonomer comprises $CF_2CF_2$; and
the fluorinated compound comprises a fluoropolymer product of polymerized $CF_2CF_2$.

42. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein the fluorinated compound has a lower global warming potential than the saturated hydrofluorocarbon.

43. A process comprising converting a saturated hydrofluorocarbon into a fluorinated compound, wherein the saturated hydrofluorocarbon comprises from 1 to 3 carbon atoms and the fluorinated compound comprises from at least 2 to 6 carbon atoms, wherein the fluorinated compound has a lower ozone depletion potential than the saturated hydrofluorocarbon.

* * * * *